(12) United States Patent
O'Neill

(10) Patent No.: US 7,484,940 B2
(45) Date of Patent: Feb. 3, 2009

(54) PIEZOELECTRIC FLUID PUMP

(75) Inventor: Conal O'Neill, Livermore, CA (US)

(73) Assignee: Kinetic Ceramics, Inc., Hayward, CA (US)

( * ) Notice: Subject to any disclaimer, the term of this patent is extended or adjusted under 35 U.S.C. 154(b) by 292 days.

(21) Appl. No.: 10/833,838

(22) Filed: Apr. 28, 2004

(65) Prior Publication Data
US 2005/0244288 A1    Nov. 3, 2005

(51) Int. Cl.
F04B 17/00    (2006.01)
(52) U.S. Cl. ............... 417/413.2; 417/413.1; 417/410.1
(58) Field of Classification Search .............. 417/413.2, 417/413.1, 410.1
See application file for complete search history.

(56) References Cited

U.S. PATENT DOCUMENTS

| | | | | |
|---|---|---|---|---|
| 4,098,560 A | | 7/1978 | O'Neill ..................... 417/214 |
| 4,231,287 A | * | 11/1980 | Smiley ........................ 92/94 |
| 4,983,876 A | | 1/1991 | Nakamura ................. 310/328 |
| 5,192,197 A | | 3/1993 | Culp ........................ 417/322 |
| 5,215,446 A | | 6/1993 | Takahashi .................. 417/322 |
| 5,267,836 A | | 12/1993 | Culp ......................... 417/52 |
| 5,597,292 A | | 1/1997 | Rhee ........................ 417/322 |
| 5,630,709 A | | 5/1997 | Bar-Cohen ................ 417/322 |
| 5,674,226 A | * | 10/1997 | Doherty et al. ............. 606/107 |
| 5,759,014 A | | 6/1998 | Van Lintel ............... 417/413.3 |
| 5,759,015 A | | 6/1998 | Van Lintel ................. 417/322 |
| 5,769,608 A | | 6/1998 | Seale ......................... 417/53 |
| 5,798,600 A | | 8/1998 | Sager ........................ 310/330 |
| 5,816,780 A | | 10/1998 | Bishop ...................... 417/322 |
| 5,876,187 A | | 3/1999 | Forster ...................... 417/322 |
| 5,906,481 A | | 5/1999 | Ogawa .................... 417/413.2 |
| 5,961,298 A | | 10/1999 | Bar-Cohen ................ 417/322 |
| 5,961,305 A | | 10/1999 | Eek ........................... 417/566 |
| 6,033,191 A | | 3/2000 | Kamper ..................... 417/322 |
| 6,042,345 A | | 3/2000 | Bishop ...................... 417/322 |

(Continued)

FOREIGN PATENT DOCUMENTS

WO    WO/0222358 A1 *  3/2002

OTHER PUBLICATIONS

MEMS Passive Check Valve, Presented Sep. 18, 2002 by Lee, Shin, and Carman. Mechanical & Aerospace Engineering Department UCLA.*

(Continued)

*Primary Examiner*—Devon C Kramer
*Assistant Examiner*—Peter J Bertheaud
(74) *Attorney, Agent, or Firm*—John R. Ross; John R. Ross, III

(57) ABSTRACT

A compact, high capacity pump for pumping fluid. A first one-way valve is between an inlet port and the pump's fluid chamber. A second one-way valve is between the pump's fluid chamber and an outlet port. A diaphragm separates a piezoelectric stack from the fluid chamber. A power source provides power to the piezoelectric stack causing it to expand and contract. The expansion and contraction of the piezoelectric stack causes fluid to be pumped from the inlet port to the fluid chamber through the first one-way valve and causes fluid to be pumped from the fluid chamber to the outlet port through the second one-way valve. In one preferred embodiment, both one-way valves are disc valves. In another preferred embodiment both one-way valves are MEMS valves.

7 Claims, 9 Drawing Sheets

U.S. PATENT DOCUMENTS

| | | | |
|---|---|---|---|
| 6,071,088 A | 6/2000 | Bishop | 417/322 |
| 6,164,933 A * | 12/2000 | Tani et al. | 417/413.2 |
| 6,554,591 B1 * | 4/2003 | Dai et al. | 417/505 |
| 6,590,267 B1 * | 7/2003 | Goodwin-Johansson et al. | 257/415 |
| 2001/0043450 A1 * | 11/2001 | Seale et al. | 361/160 |
| 2001/0043873 A1 | 11/2001 | Hironaka | 417/415 |
| 2002/0114716 A1 | 8/2002 | Takagi | 417/413.2 |
| 2002/0164255 A1 | 11/2002 | Burr et al. | 417/363 |
| 2003/0012666 A1 | 1/2003 | Takeuchi | 471/322 |
| 2003/0017063 A1 * | 1/2003 | Komatsu et al. | 417/413.2 |
| 2004/0037718 A1 * | 2/2004 | Xie et al. | 417/413.2 |

OTHER PUBLICATIONS

Journal of Microelectromechanical Systems, vol. 7, No. 4, Dec. 1998, pp. 395-403.

* cited by examiner

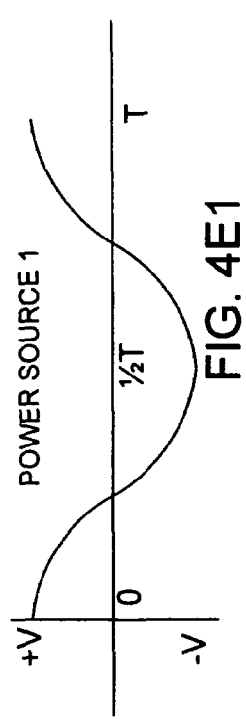
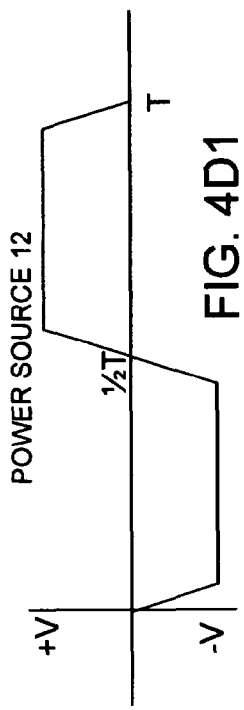
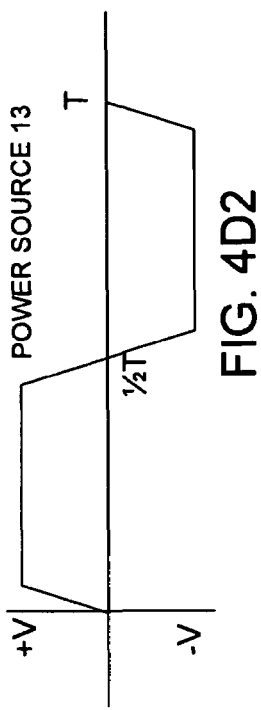
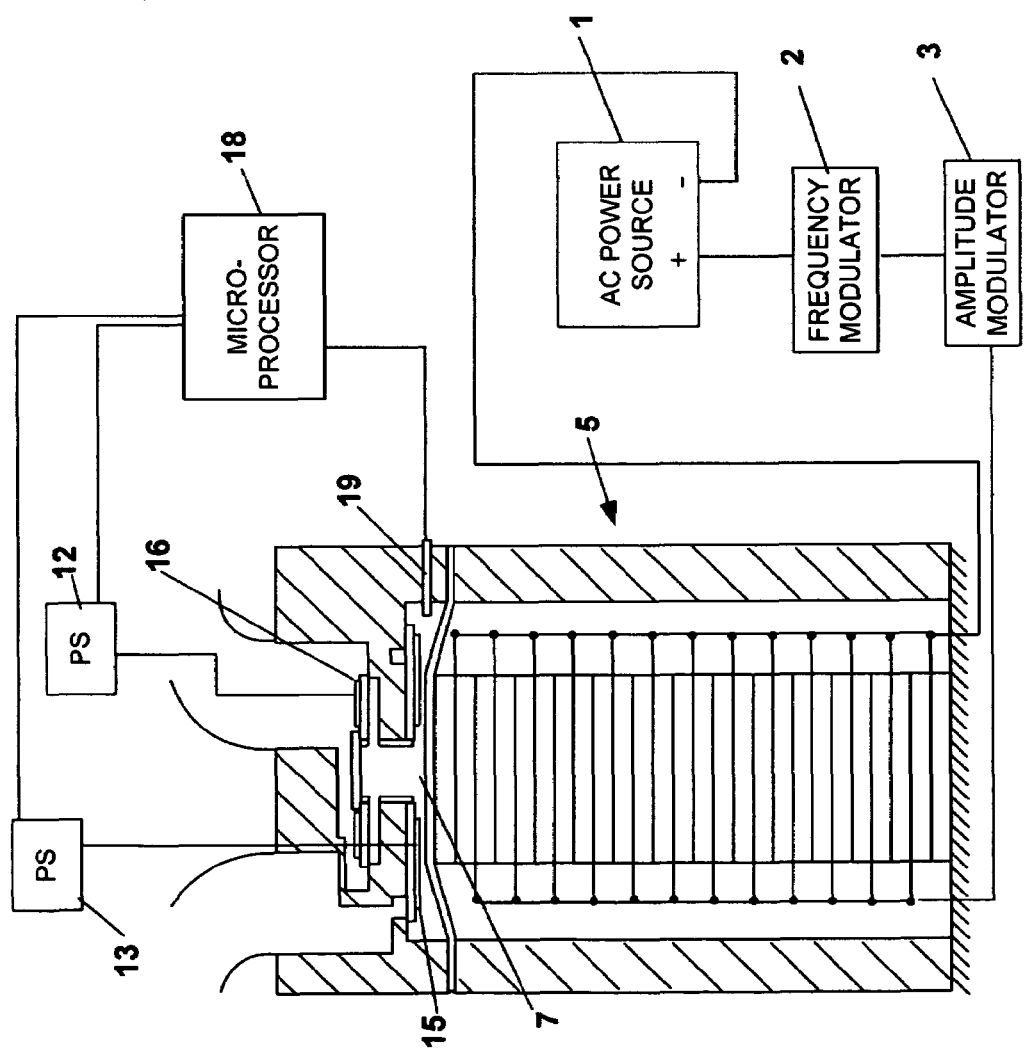

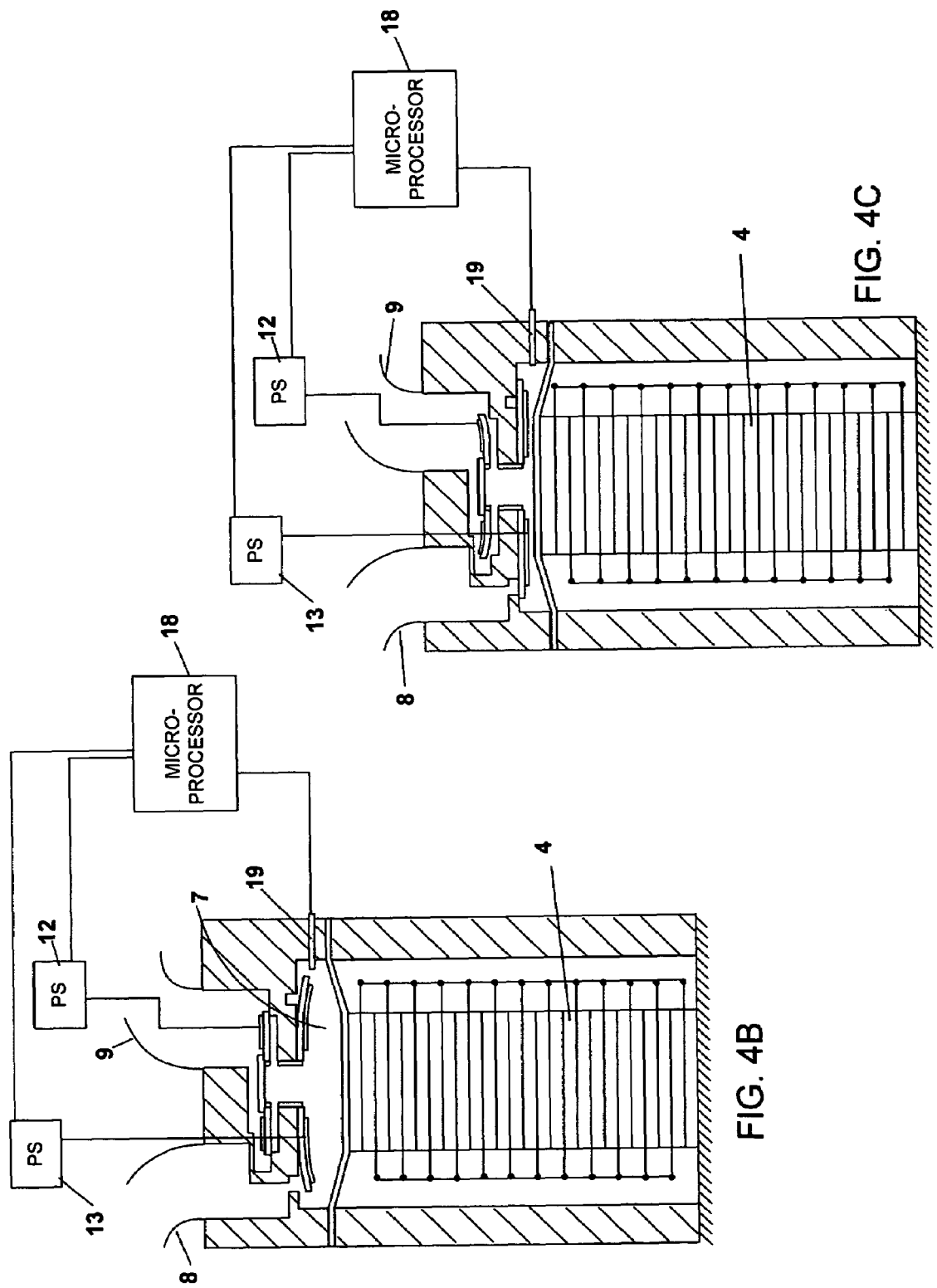

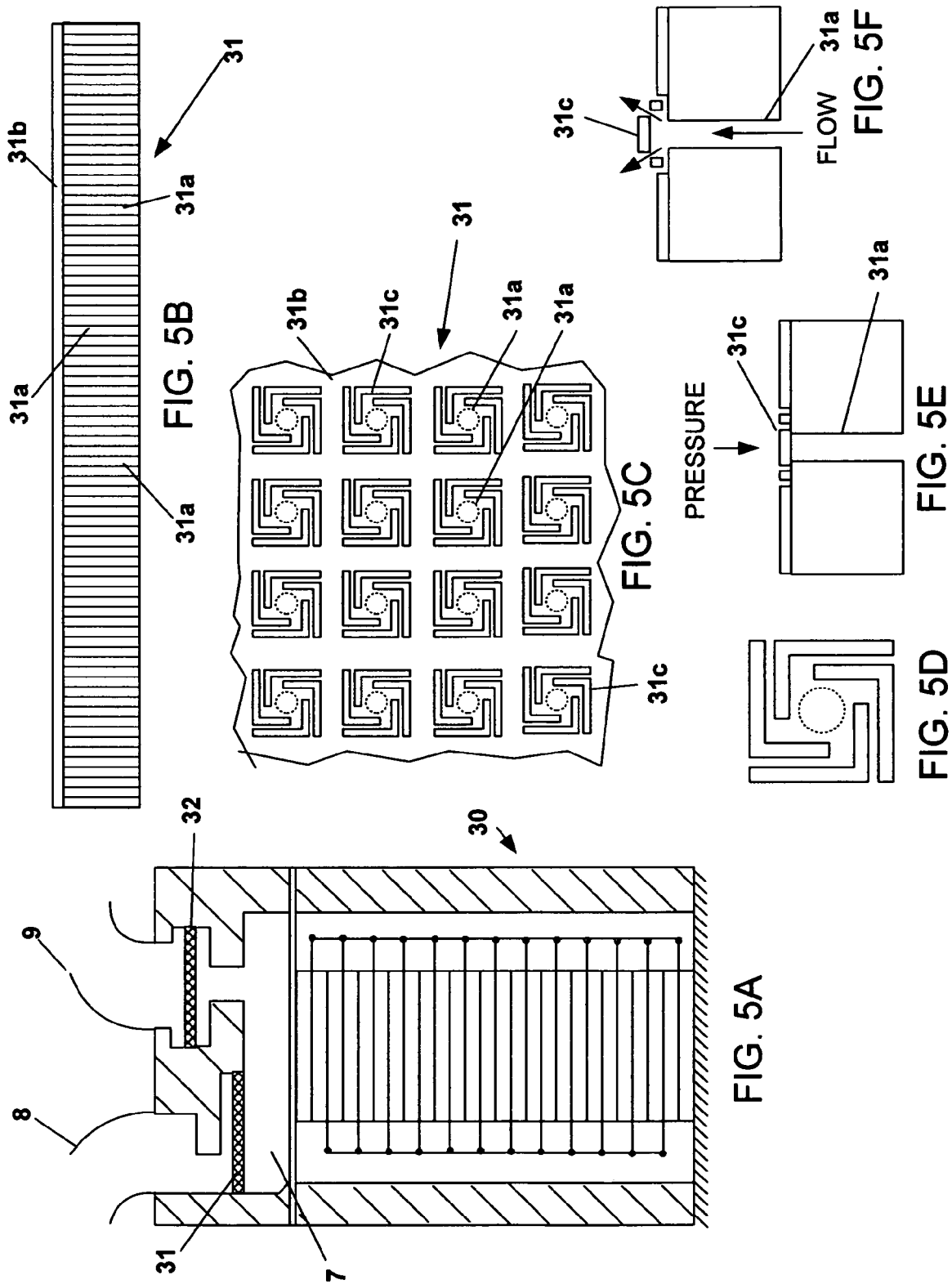

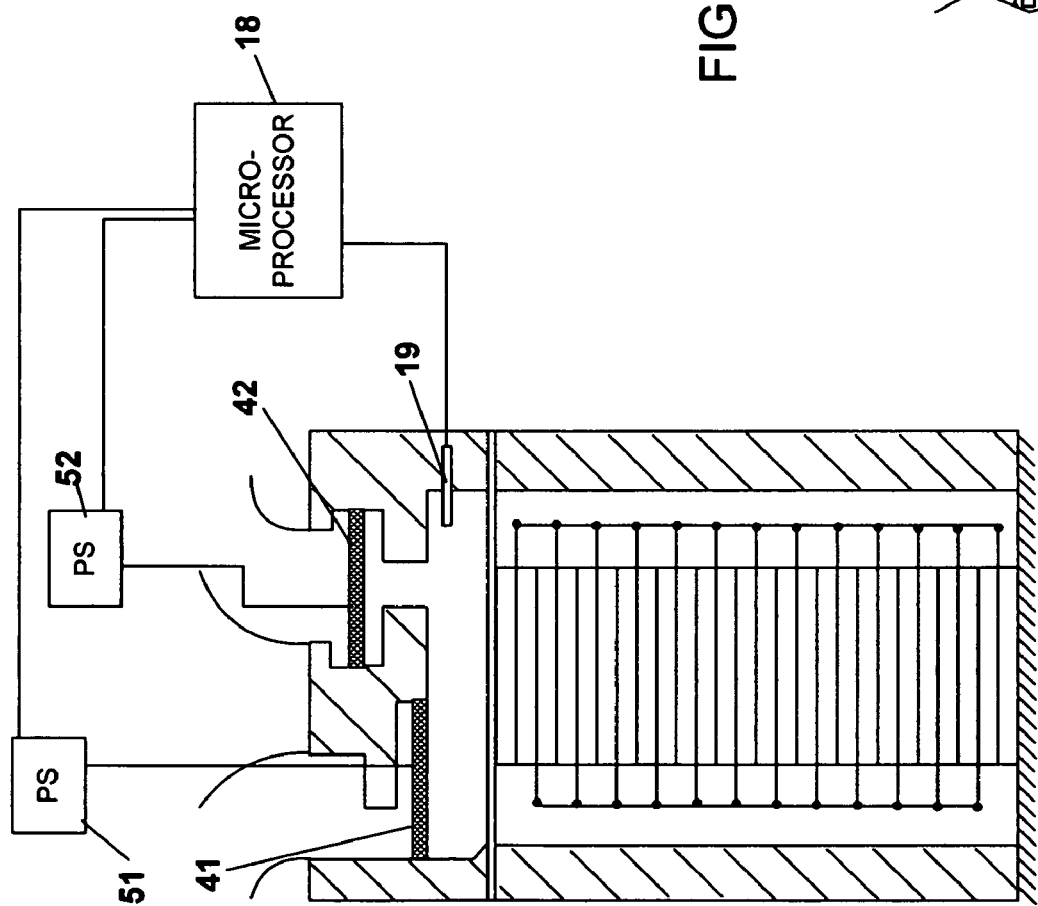
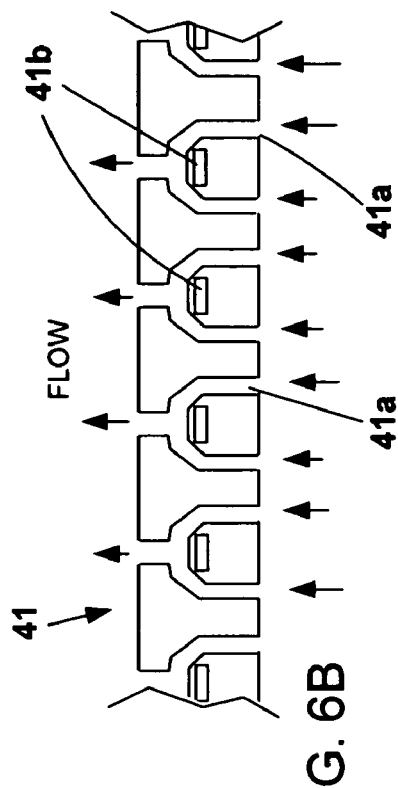
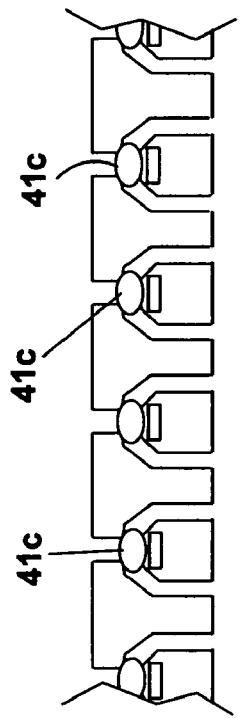
FIG. 6A
FIG. 6B
FIG. 6C

PIEZOELECTRIC FLUID PUMP

The present invention relates to pumps, and in particular, to small sized high capacity piezoelectric fluid pumps. This invention was made with Government support under contract DAAH01-01-C-R046 awarded by DARPA. The Government has certain rights in this invention.

BACKGROUND OF THE INVENTION

Conventional fluid pumps are well known. Although conventional fluid pumps are readily available in both low and high capacity designs, a common feature is that they have many moving parts that create noise and vibration. Also, there are reliability and lifetime limitations due to normal wear phenomena. Furthermore, because conventional pumps have multiple parts, they tend to be large, heavy and expensive.

Micropumps, also known as miniature pumps, are pumps that are fabricated on a microchip utilizing micromachining processes. For small capacity requirements, micropumps provide improved reliability with fewer parts. For example, micropumps utilizing electroactive transducers have emerged for biomedical and metering applications where small pressures and flow rates are required and where conventional pumps are somewhat impractical. The typical capacity of a micropump may be in the range of a few nano liters per second to a few micro liters per second. Since the total fluid power output of these devices is very small, efficiency is not highly important and is generally low. The relatively low efficiency of the micropump makes massive parallel arraying of many micropumps unattractive as a way of competing with larger conventional pumps. Scaling up the size and pressure of such electroactively driven devices does not improve the efficiency and is difficult due to on-chip fabrication techniques. This class of pump is therefore not able to compete directly with larger conventional pump designs for large fluid output.

Micro Electro Mechanical System (MEMS) microvalve arrays are known and are utilized to achieve precision fluid flow control. In a microvalve array, multiple diaphragms cover multiple ports to restrict and control fluid flow. In some designs, heaters can be activated to warm and expand a closed fluid volume that in turn moves diaphragms to close and open the individual ports to achieve a desired flow. This arrangement permits precise flow rate control but is slow to respond due to thermal conduction to and from the closed fluid volume. Other activation methods, such as piezoelectric activation, can provide faster opening and closing of the ports.

What is needed is a compact, high capacity pump that has minimal moving parts, is able to handle a relatively large fluid output, and has improved operating efficiency and reliability as well as reduced weight, size and cost.

SUMMARY OF THE INVENTION

The present invention provides a compact, high capacity pump for pumping fluid. A first one-way valve is between an inlet port and the pump's fluid chamber. A second one-way valve is between the pump's fluid chamber and an outlet port. A diaphragm separates a piezoelectric stack from the fluid chamber. A power source provides power to the piezoelectric stack causing it to expand and contract. The expansion and contraction of the piezoelectric stack causes fluid to be pumped from the inlet port to the fluid chamber through the first one-way valve and causes fluid to be pumped from the fluid chamber to the outlet port through the second one-way valve. In one preferred embodiment, both one-way valves are disc valves. In another preferred embodiment both one-way valves are MEMS valves.

BRIEF DESCRIPTION OF THE DRAWINGS

FIG. 4A shows a second preferred embodiment of the present invention.

FIGS. 4B-4I illustrate the operation of the second preferred embodiment.

FIGS. 5A-5F show a third preferred embodiment of the present invention.

FIGS. 6A-6C show a fourth preferred embodiment of the present invention.

DETAILED DESCRIPTION OF THE PREFERRED EMBODIMENTS

Figure 1A:
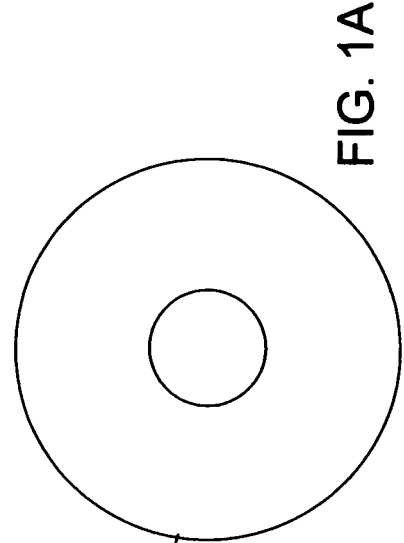
FIG. 1A shows a preferred passive disc.
Figure 1:
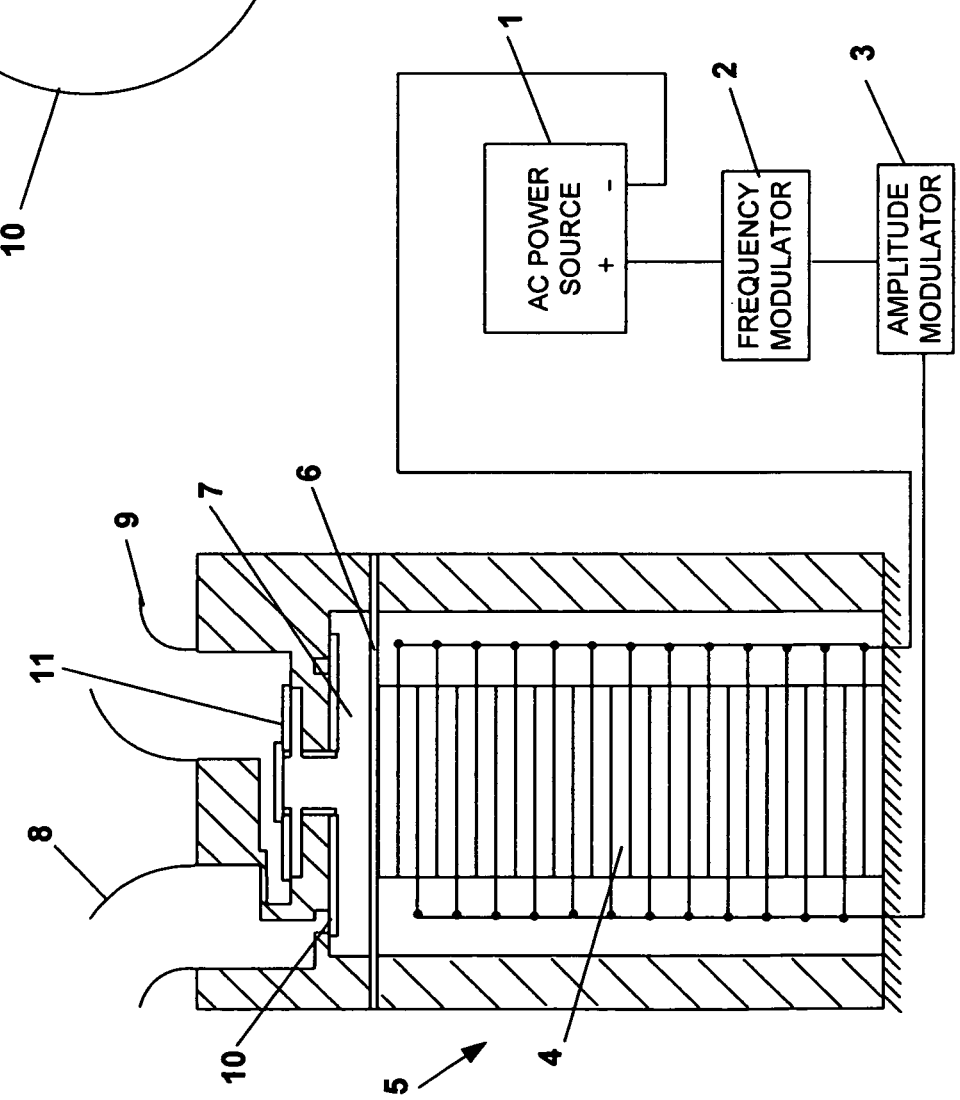
FIG. 1 shows a first preferred embodiment of the present invention.

FIGS. 1-3B disclose a first preferred embodiment of the present invention. As shown in FIG. 1, AC power source 1 provides power to piezoelectric stack 4 of piezoelectric fluid pump 5. In the preferred embodiment, pump 5 is approximately 3 inches tall, 1.5 inches diameter and weights approximately 200 grams. Frequency modulator 2 and amplitude modulator 3 are connected in series as shown and can be adjusted to vary the frequency and amplitude of the signal reaching piezoelectric stack 4. Diaphragm 6 is bonded to the top of stack 4 and separates stack 4 from fluid chamber 7. Inlet 1-way passive disc valve 10 controls the flow of fluid through inlet port 8 into fluid chamber 7. Likewise, outlet 1-way passive disc valve 11 controls the flow of fluid leaving fluid chamber 7 through outlet port 9.

Preferred Passive Disc Valve

FIG. 1A shows a top view of a preferred passive 1-way disc valves 10 (part no. J378062) and 11 (part no. J378067), both available from Kinetic Ceramics, Inc. with offices in Hayward, Calif. Passive 1-way disc valves are preferably fabricated from metal and are approximately 0.02 inches thick

Operation of the First Preferred Embodiment

As voltage is applied to stack 4 via AC power source 1, stack 4 will expand and contract in response to the AC signal, causing diaphragm 6 to bend up and down in a piston-like fashion.

Figure 2A:
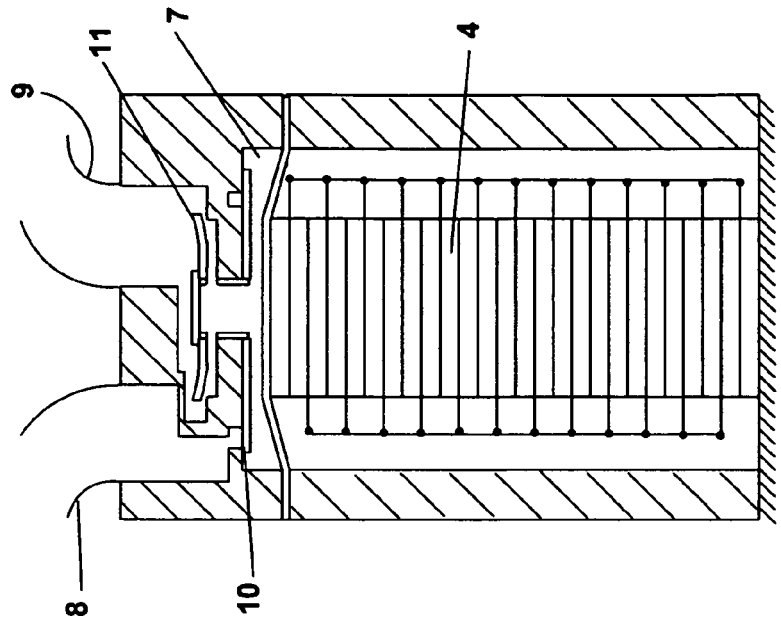
FIGS. 2A-3B illustrate the operation of the first preferred embodiment.
Figure 2B:
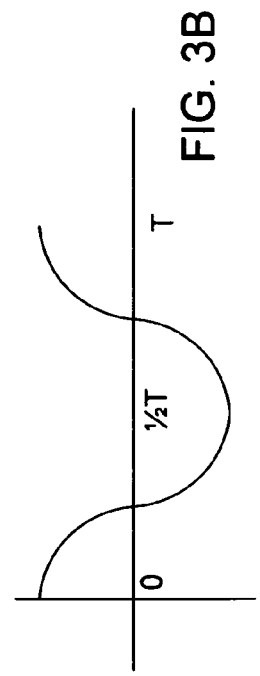

FIG. 2B shows a plot from t=0–½ T of the sine wave of the AC signal generated by AC power source 1. From t=0–½ T, stack 4 has contracted (i.e., decreased in length), see FIG. 2A. This has caused diaphragm to bend downward, thereby expanding the size of fluid chamber 7. The expanding of the size of fluid chamber 7 causes a corresponding drop in pressure inside fluid chamber 7. When the pressure inside fluid chamber 7 becomes less than the pressure inside fluid inlet port 8, 1-way passive disc valve 10 will open permitting the flow of fluid into fluid chamber 7. When the pressure inside fluid chamber 7 becomes less than the pressure inside fluid outlet port 9, 1-way passive disc valve 11 will close preventing a back flow of fluid from outlet port 9 into fluid chamber 7.

Figure 3A:
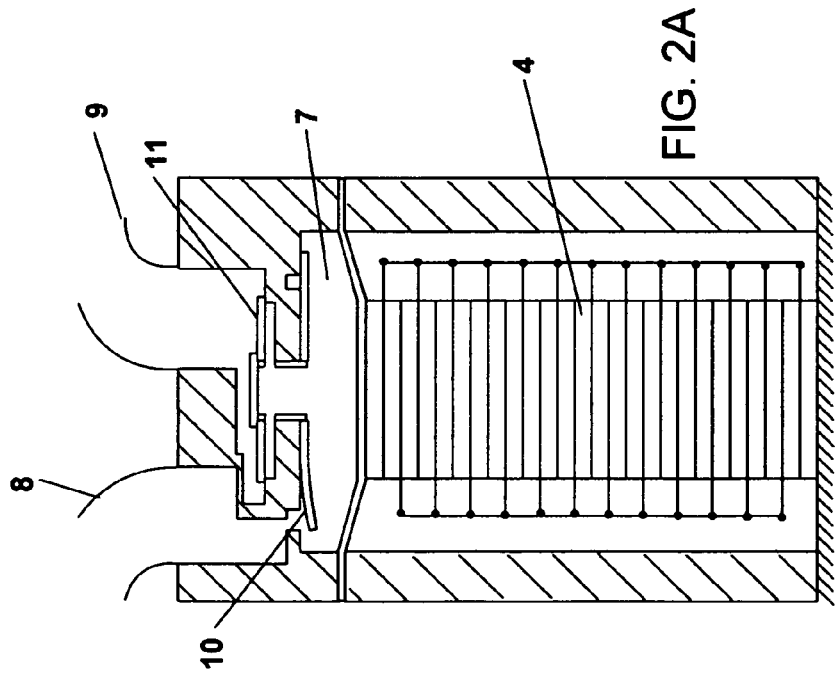
Figure 3B:
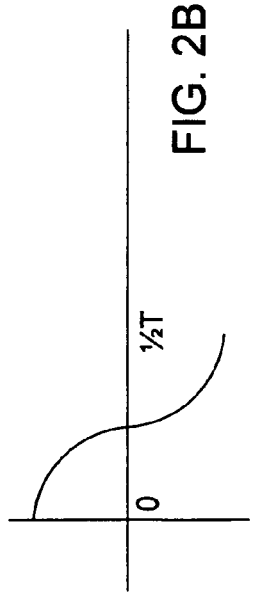

From t=½ T–T (see FIG. 3B), stack 4 has expanded (i.e., increased in length), as shown in FIG. 3A. This has caused diaphragm to bend upward, thereby decreasing the size of fluid chamber 7. The decreasing of the size of fluid chamber 7 causes a corresponding increase in pressure inside fluid chamber 7. When the pressure inside fluid chamber 7 becomes greater than the pressure inside fluid outlet port 9, 1-way passive disc valve 11 will open permitting the flow of fluid into fluid chamber 7. When the pressure inside fluid chamber 7 becomes greater than the pressure inside fluid inlet port 8, 1-way passive disc valve 10 will close preventing a back flow of fluid from fluid chamber 7 into inlet port 8.

In this fashion, piezoelectric fluid pump 5 will continue to pump fluid from inlet port 8 to outlet port 9 until AC power source 1 is removed.

Applicant built and tested a prototype of the first preferred embodiment and achieved an output power of approximately 0.1 horsepower. In comparison it is estimated that a conventional pump capable of operating at the same or similar capacity would have many more parts and would weigh 2 to 4 Kg.

Second Preferred Embodiment

A second preferred embodiment is disclosed by reference to FIGS. 4A-4E. In the second preferred embodiment, 1-way active disc valves 15 and 16 have replaced 1-way passive disc valves 10 and 11 of the first preferred embodiment. 1-way active disc valves 15 and 16 are electrically connected to AC power sources 12 and 13 as to open and close based on electrical signals.

Preferred Active Disc Valves

Figure 4G:
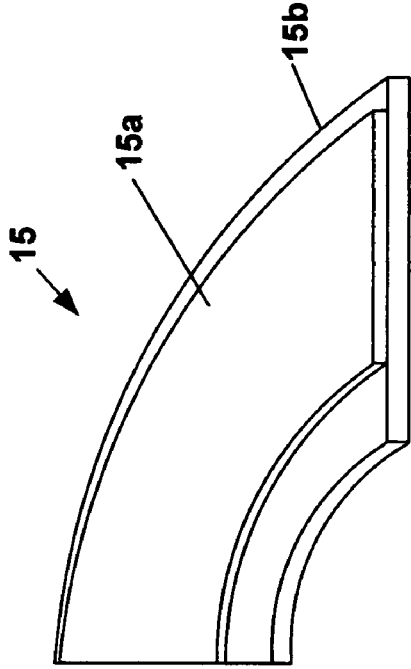
Figure 4I:
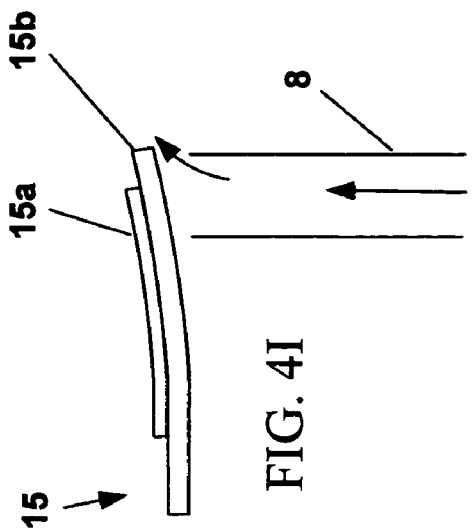
Figure 4H:
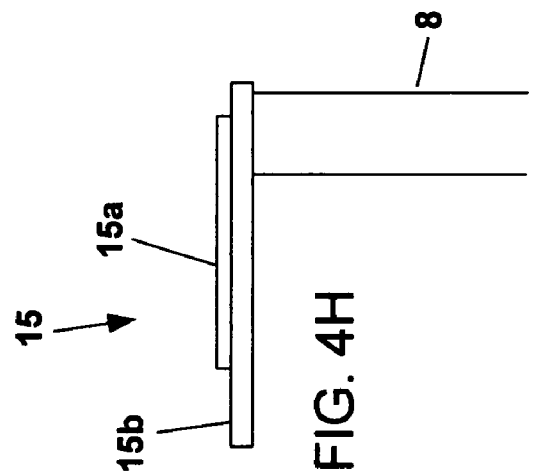
Figure 4F:
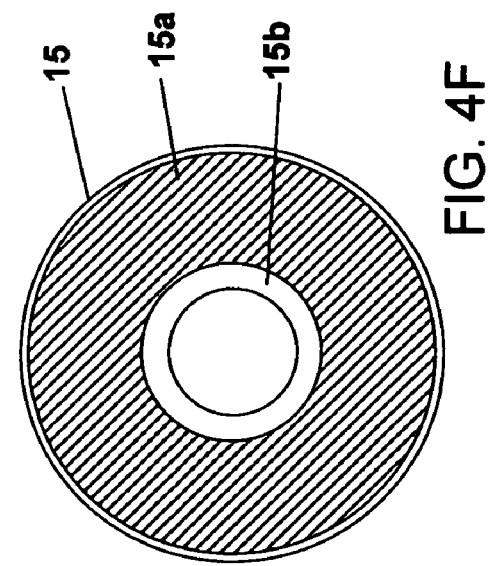

FIG. 4F shows a top view of active disc valve 15 and FIG. 4G shows a perspective ¼ cutout section of active disc valve 15. Piezoelectric actuator 15a is bonded to the top of metal disc valve 15b. Piezoelecrtric actuator 15a utilizes the $d_{31}$ piezoelectric mode of operation ($d_{31}$ describes the strain perpendicular to the polarization vector of the ceramics).

Operation of Active Disc Valves

FIGS. 4H and 4I illustrate the operation of the preferred active disc valve. In FIG. 4H no electricity has been applied to the piezoelectric actuator 15a and metal disc valve 15b is sealing flow inlet port 8. In FIG. 4I, electricity has been applied to piezoelectric actuator and it has contracted causing metal disc valve 15b to bend thereby breaking the seal over inlet port 8. Fluid can now flow through the valve.

Operation of the Second Preferred Embodiment

In FIG. 4A, t=0 (FIG. 4E1) and the voltage output of AC power source 1 is at a maximum. 1-way active disc valve 16 is closing in response to power source 12 and 1-way active disc valve 15 is opening in response to power source 13.

In FIG. 4B, 0<t<½ T (FIG. 4E1) and the voltage output of AC power source 1 is a negative going sine function. Voltage from AC power source 1 has caused stack 4 to contract bending diaphragm 6 downward resulting in a pressure drop in fluid chamber 7. Pressure sensor 19 has sensed a decrease in pressure inside pumping chamber 7 and has sent a signal to microprocessor 18. Microprocessor 18 has sent a control signal to power sources 12 and 13 causing them to transmit control voltages to 1-way active disc valves 16 and 15, respectively. The positive voltage from AC power source 13 (FIG. 4D2) has caused 1-way active disc valve 15 to open and the negative voltage from power source 12 (FIG. 4D1) has caused 1-way active disc valve 16 to remain closed. Fluid from inlet port 8 has entered pumping chamber 7.

In FIG. 4C, ½ T<t<T, the voltage output of AC power source 1 is a positive going sine function (FIG. 4E1), causing stack 4 to expand bending diaphragm 6 upward and resulting in a pressure increase in fluid chamber 7. Pressure sensor 19 has sensed a an increase in pressure inside pumping chamber 7 and has sent a signal to microprocessor 18. Microprocessor 18 has sent control signals to power sources 12 and 13 causing them to transmit control voltages to 1-way active disc valves 16 and 15, respectively. The negative voltage from AC power source 13 has caused 1-way active. disc valve 15 to close and the positive voltage from AC power source 12 has caused 1-way active disc valve 16 to open. Fluid from pumping chamber 7 has entered outlet port 9.

At time t=T (FIG. 4E1), the voltage output of AC power source 1 is again at a maximum and stack 4 is at a fully expanded condition, as shown in FIG. 4A. 1-way active disc valve 15 is opening in response to power source 13 and 1-way active disc valve 16 is closing in response to power source 12 preventing fluid from flowing back to fluid chamber 7 through 1-way active disc valve 16. In this fashion, piezoelectric fluid pump 5 will continue to pump fluid from inlet port 8 to outlet port 9 until AC power sources 1, 12, and 13 are removed.

In this fashion, piezoelectric fluid pump 5 will continue to pump fluid from inlet port 8 to outlet port 9 until AC power source 1 is removed.

Due to the fast response of the piezoelectric active disc valve, the pump actuator can be cycled faster than it could with the passive disc valve. This will allow for more pump strokes per second and an increase in pump output.

Third Preferred Embodiment

MEMS Valves

A third preferred embodiment is disclosed by reference to FIGS. 5A-5F. The third preferred embodiment utilizes two passive MEMS valve arrays.

In the third preferred embodiment, pump 30 is similar to pump 5 shown in FIG. 1, with an exception being that disc valves 10 and 11 of pump 5 have been replaced with l-way passive microvalve arrays 31 and 32, as shown in FIG. 5A. Preferably, microvalve arrays 31 and 32 are two micromachined MEMS valves.

FIG. 5B shows an enlarged side view of microvalve array 31. Microvalve array 31 is fabricated from silicon, silicone nitride or nickel and includes an array of fluid flow ports 31a approximately 200 microns in diameter. The array of fluid flow ports 31a is covered by diaphragm layer 31b. FIG. 5C shows an enlarged top view of a cutout portion of microvalve array 31. Microvalve array 31 has a plurality of diaphragms 31c covering each fluid flow port 31a.

Operation of a Microvalve Array

Microvalve arrays 31 and 32 function in a fashion similar to passive disc valves 10 and 11. In FIG. 5E, the pressure pressing downward on diaphragm 31c is greater than the pressure of fluid inside fluid flow port 31a. Therefore, diaphragm 31c seals fluid flow port 31a. Conversely, in FIG. 5F, the pressure pressing downward on diaphragm 31c is less than the pressure of fluid inside fluid flow port 31a. Therefore, diaphragm 31c is forced open and fluid flows through fluid flow port 31a.

Applying this principle to the third preferred embodiment, when the pressure inside fluid chamber 7 becomes less than the pressure inside fluid inlet port 8, individual valves within the multitude of microvalves in microvalve array 31 will open permitting the flow of fluid into fluid chamber 7. When the pressure inside fluid chamber 7 becomes less than the pressure inside fluid outlet port 9, the individual valves within the multitude of micro valves in the microvalve array 32 will close preventing a back flow of fluid from outlet port 9 into fluid chamber 7.

Likewise, when the pressure inside fluid chamber 7 becomes greater than the pressure inside fluid outlet port 9, the individual valves within the multitude of micro valves in microvalve array 32 will open permitting the flow of fluid into outlet port 9. When the pressure inside fluid chamber 7 becomes greater than the pressure inside fluid inlet port 8, the individual valves within the multitude of micro valves in microvalve array 31 will close preventing a back flow of fluid from fluid chamber 7 into inlet port 8.

Due to its small size and low inertia, the microvalve array can respond quickly to pressure changes. Therefore, pump output is increased because it can cycle faster than it could with a more massive valve Fourth Preferred Embodiment Active MEMS Valve Operation A fourth preferred embodiment is similar to the second preferred embodiment described above in reference to FIGS. 4A-4E, with the exception that active disc valves 15 and 16 (FIG. 4A) are replaced with active microvalve arrays 41 and 42 (FIG. 6A).

FIG. 6B shows an enlarged side view of microvalve array 41. Microvalve array 41 is fabricated from silicon and includes an array of "Y" shaped fluid flow ports 41a approximately 200 microns in diameter. Preferably, microvalve array 42 is identical to microvalve array 41. Below the junction of each "Y" are heaters 41b. Heaters 41b for microvalve array 41 are electrically connected to power source 51 and heaters 41b for microvalve array 42 are electrically connected to power source 52. Pressure sensor 19 senses the pressure inside fluid chamber 7 and sends a corresponding signal to microprocessor 18. Microprocessor 18 is configured to send control signals to power sources 51 and 52.

Operation of an Active Microvalve Array

Microvalve arrays 41 and 42 function in a fashion similar to active disc valves 15 and 16. For example, in FIG. 6B active microvalve array 41 is open. Fluid is able to flow freely through fluid flow ports 41a. In FIG. 6C, microvalve array 41 is closed. Power source 51 has sent voltage to heaters 41b of microvalve array 41. Heaters 41b have heated the adjacent fluid causing a phase change to a vapor phase and the formation of high pressure bubbles 41c. High pressure bubbles 41c block fluid flow ports 41a for a short time closing microvalve array 41. The lack of mass or inertia due to there being no valve diaphragm permits very fast response which enables the valves to open and close at high a frequency beyond 100 kHz.

Applying this principle to the third preferred embodiment, when piezoelectric stack 4 contracts and the pressure inside fluid chamber 7 becomes less than the pressure inside fluid inlet port 8, pressure sensor 19 will send a corresponding signal to microprocessor 18. Microprocessor 18 will then send a control signal to power sources 51 and 52. Consequently, individual valves within the multitude of microvalves in microvalve array 41 will open permitting the flow of fluid into fluid chamber 7 (FIG. 6B). Also, individual valves within the multitude of micro valves in the microvalve array 42 will close (FIG. 6C) preventing a back flow of fluid from outlet port 9 into fluid chamber 7.

Likewise, when piezoelectric stack 4 expands and the pressure inside fluid chamber 7 becomes greater than the pressure inside fluid outlet port 9, pressure sensor 19 will send a corresponding signal to microprocessor 18. Microprocessor 18 will then send control signals to power sources 51 and 52. Consequently, the individual valves within the multitude of micro valves in microvalve array 42 will open permitting the flow of fluid into outlet port 9. Also, the individual valves within the multitude of micro valves in microvalve array 41 will close preventing a back flow of fluid from fluid chamber 7 into inlet port 8.

Due to its ability to anticipate the need to open and close, the active microvalve array can respond very quickly. Hence, the pump can cycle faster and pump output is increased.

Fifth Preferred Embodiment

Resonant Operation

The fifth preferred embodiment recognizes that at certain frequencies generated by AC source 1, stack 4 will resonate. As stack 4 resonates, the amount of electrical energy required to displace stack 4 by a given amount will decrease. Therefore, the efficiency of the piezoelectric pump will be increased.

Any electromechanical spring/mass system (including piezoelectric stack 4) will resonate at certain frequencies. The "primary" or "first harmonic" frequency is the preferred frequency. In the fifth preferred embodiment, AC power source 1 sends an electrical drive signal to the piezoelectric stack 4 at or near the primary resonant frequency. That frequency is calculated by using the mass and modulus of elasticity for the piezoelectric stack: $f=sqrt(k/m)$ where m is the mass of the resonant system and k is the spring rate (derived from the modulus of elasticity). When in resonance, the amplitude of the motion will increase by a factor of 4 or 5. Thus for a given pump stoke, the drive voltage and electrical input power can be reduced by a similar factor.

Figure 7:
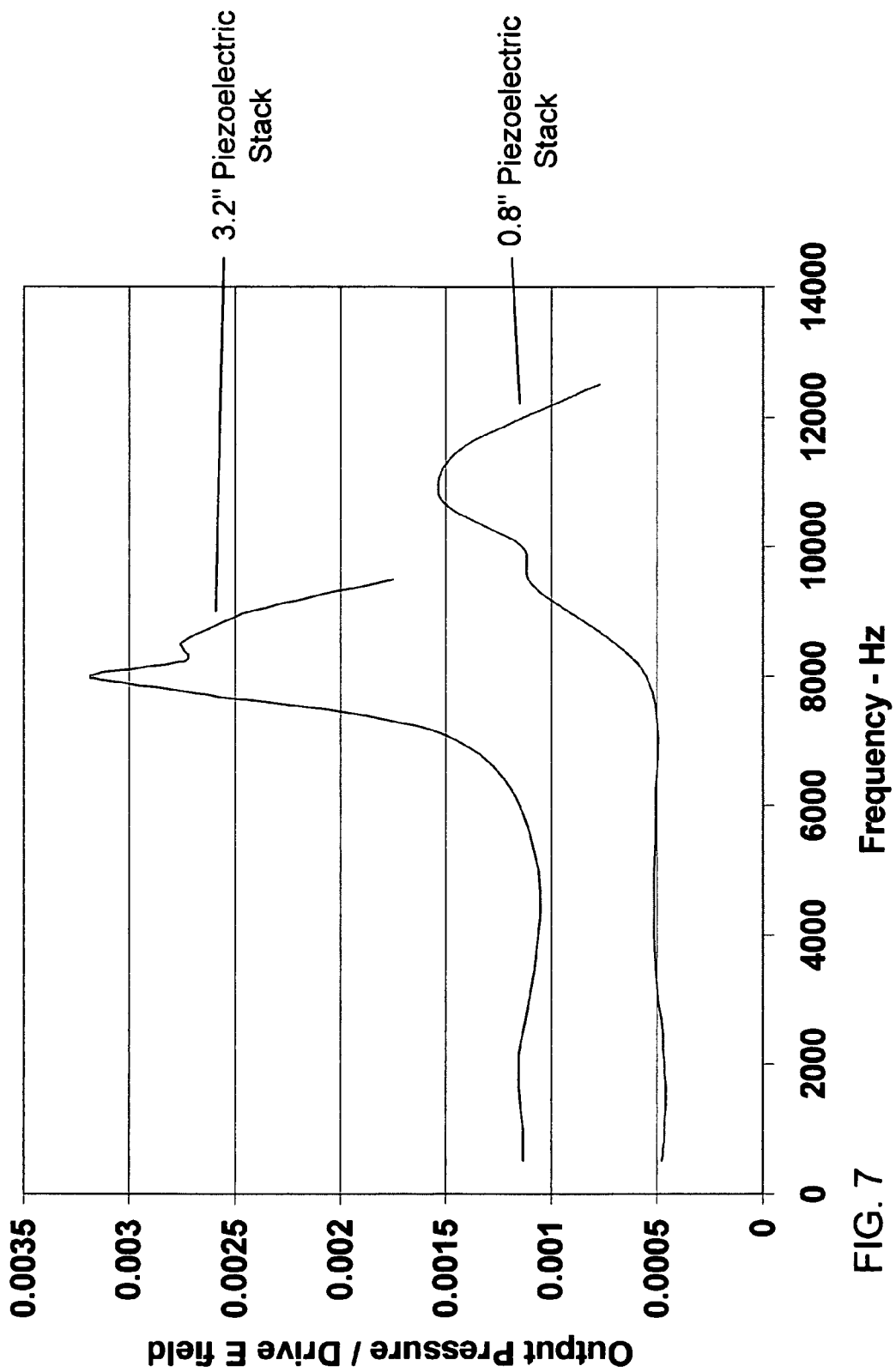
FIG. 7 is a graph of Output Pressure/E Field vs Frequency.

For example, FIG. 7 shows a graph of output pressure versus frequency for two pump configurations: A pump having a piezoelectric stack with a length of 3.2 inches, and a pump having a piezoelectric stack with a length of 0.8 inches. As can be seen by the graph, when the pump is operated so that the piezoelectric stack resonates, it is possible to achieve approximately a 300% increase in efficiency.

Utilization of the Present Invention

Figure 8:
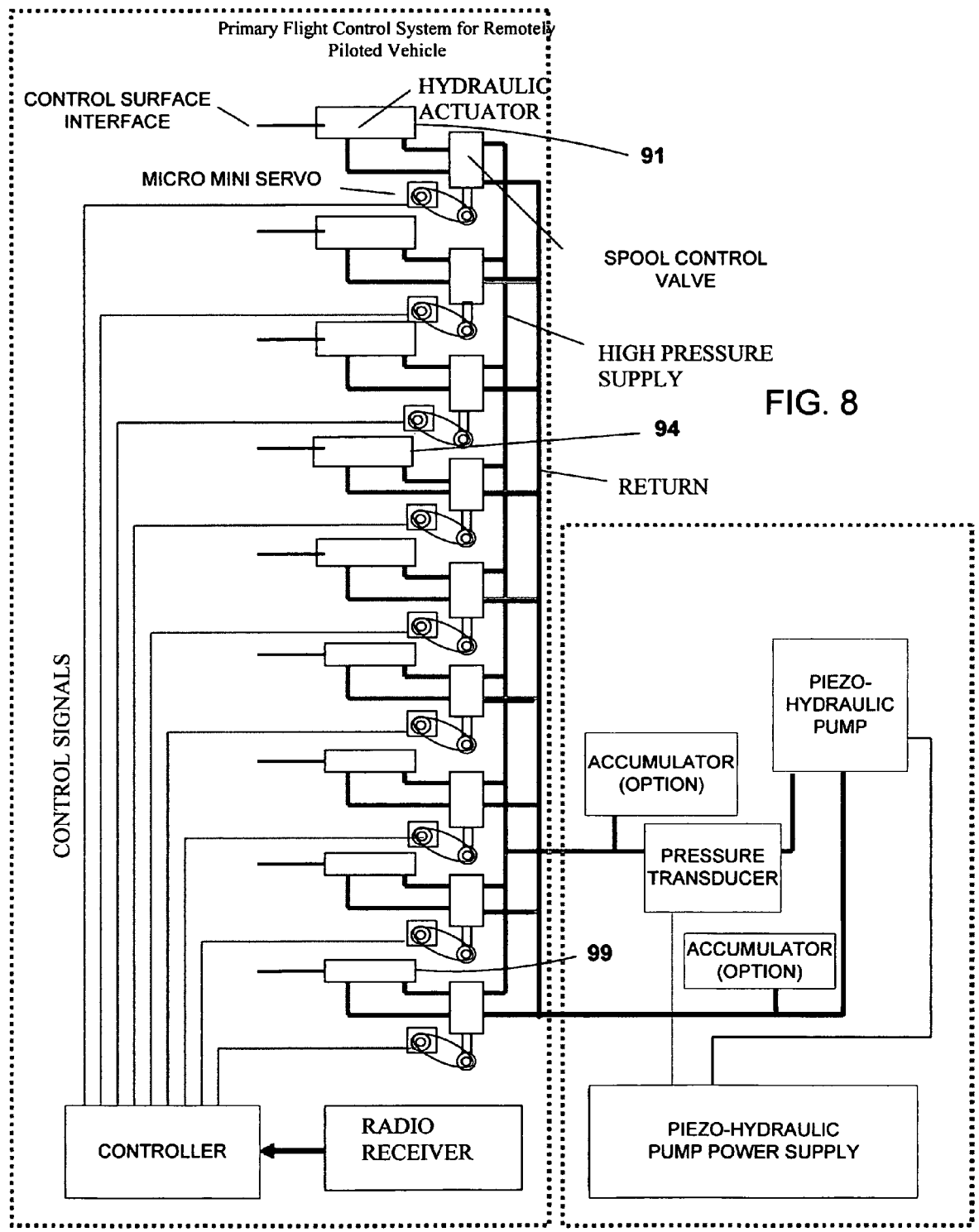
FIG. 8 presents an example of a utilization of the present invention.

The present invention can be utilized for a variety of purposes. One preferred purpose is illustrated in FIG. 8. In FIG. 8, pump 5 is utilized to pump hydraulic fluid to hydraulic actuators 91-99. The hydraulic actuators are utilized for the primary flight control system for a remotely piloted vehicle. In the preferred embodiment shown in FIG. 8, piezoelectric pump 5 pumps hydraulic fluid to hydraulic actuators 91-99 at a flow rate of up to 60 cc/second. The high hydraulic power output permits fast aircraft control surface adjustments. The combination of high power and light weight materials permits fast aircraft maneuvering that would otherwise not be feasible.

Although the above-preferred embodiments have been described with specificity, persons skilled in this art will recognize that many changes to the specific embodiments disclosed above could be made without departing from the spirit of the invention. Therefore, the attached claims and their legal equivalents should determine the scope of the invention.

What is claimed is:

1. A compact, high capacity pump, comprising:
   A) an inlet port and an outlet port,
   B) a fluid chamber,
   C) a first one-way processor controlled active valve located flow wise between said inlet port and said fluid chamber,
   D) a second one-way processor controlled active valve located flow wise between said fluid chamber and said outlet port,
   E) a piezoelectric stack,
   F) a diaphragm separating said piezoelectric stack and said fluid chamber,
   G) a power source for providing periodically varying voltage signals to said piezoelectric stack to cause expansion and contraction of said piezoelectric stack to produce fluid flow from said inlet port to said outlet port,
   H) a first power source for providing power to said first one-way valve,
   I) a second power source for providing power to said second one-way valve,
   J) a microprocessor electrically connected to said first power source and said second power source, and
   K) a pressure sensor means electrically connected to said microprocessor, said pressure sensor means for sensing the pressure inside said fluid chamber and for sending a signal to said microprocessor when said pressure sensor means senses a change in pressure inside said fluid chamber causing said microprocessor to send a control signal to said first power source and said second power source causing said first power source to open or close said first one-way valve and causing said second power source to open or close said second one-way valve.

2. The pump as in claim 1, wherein said first one-way processor controlled active valve and said second one-way processor controlled active valve are both active microvalve arrays.

3. The pump as in claim 1, wherein said first one-way processor controlled active valve and said second one-way processor controlled active valve are both active MEMS valve arrays.

4. The pump as in claim 1, wherein said piezoelectric stack is operated at resonant frequency.

5. A compact, high capacity pump, comprising:
   A) an inlet port means and an outlet port means,
   B) a fluid chamber means,
   C) a first one-way processor controlled active valve means located flow wise between said inlet port means and said fluid chamber means,
   D) a second one-way processor controlled active valve means located flow wise between said fluid chamber means and said outlet port means,
   E) a piezoelectric stack means,
   F) a diaphragm means separating said piezoelectric stack means and said fluid chamber means,
   G) a power source means for providing periodically varying voltage signals to said piezoelectric stack means to cause expansion and contraction of said piezoelectric stack means to produce fluid flow from said inlet port means to said outlet port means,
   H) a first power source means for providing power to said first one-way processor controlled active valve means,
   I) a second power source means for providing power to said second one-way processor controlled active valve means,
   J) a microprocessor means electrically connected to said first power source means and said second power source means,
   K) a pressure sensor means electrically connected to said microprocessor means, said pressure sensor means for sensing the pressure inside said fluid chamber means and for sending a signal to said microprocessor means when said pressure sensor senses a change in pressure inside said fluid chamber means causing said microprocessor means to send a control signal to said first power source means and said second power source means causing said first power source means to open or close said first one-way processor controlled active valve means and causing said second power source means to open or close said second one-way processor controlled active valve means.

6. The pump as in claim 5, wherein said first one-way processor controlled active valve means and said second one-way processor controlled active valve means are both active microvalve array means.

7. The pump as in claim 5, wherein said first one-way processor controlled active valve means and said second one-way processor controlled active valve means are both active MEMS valve array means.

* * * * *